(12) United States Patent
Peterman

(10) Patent No.: US 8,414,755 B2
(45) Date of Patent: Apr. 9, 2013

(54) MICROFLUIDIC SEPARATION DEVICE

(75) Inventor: Mark C. Peterman, Fremont, CA (US)

(73) Assignee: OndaVia, Inc., Hayward, CA (US)

( * ) Notice: Subject to any disclaimer, the term of this patent is extended or adjusted under 35 U.S.C. 154(b) by 258 days.

(21) Appl. No.: 12/455,256

(22) Filed: May 29, 2009

(65) Prior Publication Data

US 2010/0300883 A1 Dec. 2, 2010

(51) Int. Cl.
*G01N 27/26* (2006.01)

(52) U.S. Cl.
USPC .......... 204/603; 204/600; 204/601; 204/643; 435/287.2; 435/288.7; 422/82.05; 422/82.06; 422/82.07; 422/82.08

(58) Field of Classification Search ............ 204/600, 204/601, 603, 643; 435/287.2, 288.7; 422/82.05, 422/82.06, 82.07, 82.08

See application file for complete search history.

(56) References Cited

U.S. PATENT DOCUMENTS

| | | | |
|---|---|---|---|
| 6,448,064 | B1 | 9/2002 | Vo-Dinh et al. |
| 7,267,948 | B2 | 9/2007 | Vo-Dinh et al. |
| 2004/0035701 | A1* | 2/2004 | Han et al. ............. 204/451 |
| 2004/0142484 | A1 | 7/2004 | Berlin et al. |
| 2005/0221333 | A1 | 10/2005 | Sundararajan et al. |
| 2005/0233474 | A1 | 10/2005 | Roitman et al. |
| 2007/0017812 | A1 | 1/2007 | Bousse |

\* cited by examiner

*Primary Examiner* — Bruce Bell
(74) *Attorney, Agent, or Firm* — Lumen Patent Firm

(57) ABSTRACT

A microfluidic separation device is provided that includes a sample channel having a first sample channel region and a second sample channel region, where a cross-section of the first sample channel region is smaller than a cross-section of the second sample channel region. The invention further includes a detection region having a first detection region and a second detection region, where a cross-section of the first detection region is larger than a cross-section of the second detection region and the second sample channel region is connected to the first detection region. Additionally, the invention includes a marker input channel disposed to input markers into the second sample channel region, where the markers are larger than the cross-section of the first sample channel region and the cross-section of the second detection region, where the markers collect in the first detection region.

6 Claims, 4 Drawing Sheets

(a)

(b)

MICROFLUIDIC SEPARATION DEVICE

FIELD OF THE INVENTION

The invention relates generally microfluid separation devices. More particularly, the invention relates to a microfluid separation device having narrow channels to trap signal-enhanced particles at a detection region within a longer separation channel.

BACKGROUND

The residential drinking water for forty-one million Americans in twenty-four major metropolitan areas contains pharmaceutical compounds. The human health effects of long-term, chronic exposure to trace levels of these hormones, endocrine-disrupting compounds, painkillers, and antibiotics are not yet fully understood, although the impact on aquatic life has been observed as changes in reproductive health and function. The importance of this potential threat to human health is the subject of much recent research and investigation highlighted by two late-2008 conferences sponsored by the National Institute of Environmental Health Sciences regarding pharmaceuticals and personal care products in the environment.

These compounds are present at minute, yet potentially significant, concentrations. Existing tools that can measure these very low concentrations—e.g., liquid chromatography with mass spectroscopy (LC-MS)—are expensive, complex, laboratory-based instruments. Current portable monitoring tools cannot even approach measuring parts per billion, let alone the parts-per-trillion levels of pharmaceuticals found in drinking water. At the same time, our water sources are threatened by numerous other pollutants with regulatory limits at the parts-per-billion level: agricultural run-off, heavy metals, military remnants, and industrial waste. The ability to monitor our water supply at the parts-per-billion level at the source or in the field would vastly improve the capabilities of water suppliers. This ability will in turn allow water suppliers to increase monitoring frequency, to implement remediation steps, and to focus research efforts on understanding of the health effects of chronic exposure.

Laboratory detection equipment such as embedded surface-enhanced Raman spectroscopy (eSERS) can address this deficiency by measuring compounds in aqueous solution at better than one part per billion. This embedded detection approach relies upon geometric constraints within a microfluidic channel to trap gold nanoparticles, creating a region of extreme nanoparticle density—i.e., maximum surface area in a minimum volume—required for the eleven to fifteen order-of-magnitude enhancement of Raman signal.

The presence of pharmaceuticals in the environment has been documented since the 1980s. Recent surveillance studies have brought this concern to the forefront, highlighting the widespread impact upon the US population. It has been reported that at least 41 million Americans across 24 major metropolitan areas have detectable levels of pharmaceuticals in their drinking water. Multiple US Geological Survey studies and reports since the late 90's have demonstrated the presence of contaminants in ground and surface water. Moreover, the NIEHS sponsored two late-2008 conferences regarding pharmaceuticals and personal care products in the environment, the US EPA launched Information Collection Request for health care facilities regarding unused pharmaceuticals, and the National Academy of Sciences had a December 2008 workshop on screening risk from pharmaceuticals in drinking water.

The health effects of these trace compounds on humans are not well understood, although reports regarding the impact on non-target species are widely known. Many fish experience reproductive problems, with male fish producing female proteins and female fish growing male reproductive organs. In some locations downstream from wastewater treatment facilities, the ratio of males to females is wildly skewed, even though the populations are normal upstream.

The challenge with understanding the health effect on humans is the time-scale at which an effect might occur and the wide range of potential contaminants at minute concentrations over a large area. A recent study found 34 pharmaceuticals and other organic wastewater contaminants in a New Jersey stream downstream from a wastewater-treatment facility. These chemicals included antibiotics (triclosan and sulfamethoxazole), nicotine metabolites (cotinine), decongestants (diphenhydramine), and analgesics (acetaminophen). Philadelphia discovered 56 pharmaceuticals and by-products in treated drinking water, including epilepsy and mental illness medications in the tens of parts per trillion range.

Pharmaceuticals are not the only contaminant of concern in drinking water; the total number of potential contaminants is staggering. Industrial waste and agricultural run-off are both frequently detected in surface water, with levels regulated by the EPA. Some compounds are widely used in industrial or agricultural settings, such as atrazine to control broadleaf weeds—which has been reported to cause reproductive problems in non-target species (including humans). Some compounds may be intentionally added to food or water, such as the addition of melamine to infant formula—a chemical that has been added nefariously to Chinese products and inadvertently to American products. Other compounds leach from storage containers, such as bisphenol A (BPA) from plastic bottles. A portable instrument that could measure these compounds at the part-per-billion level would be valuable to water suppliers, regulators, and consumers world-wide to maintain safe supplies, increase monitoring frequency and accuracy, and provide comfort that our water is safe to drink.

The first line of defense for protecting the water supply—and ultimately, human health—from pharmaceuticals and other contaminants is tools to rapidly and accurately measure trace levels of compounds in the field or at the source. Unfortunately, water analysis at the required accuracy with a portable instrument is currently not possible. Current portable instruments either measure overall water quality or measure water constituents. Tools that measure water quality focus on pH, turbidity, and total dissolved solids to provide a generic measure of water cleanliness. These tools are valuable for the speed at which they provide confidence, but do not measure actual water contaminants. Tools that measure water constituents primarily focus on UV/vis spectrometry or colorimetry. Both analytical methods are limited to measuring parts per million, far from the regulatory limits of many compounds, and even farther from the concentration of pharmaceuticals in drinking water.

Not only are the total number of potential contaminants staggering, but so are also the number of required analytical techniques. Analysis of specific analytes at minute levels within a water sample requires complex, expensive laboratory equipment. A variety of laboratory techniques exist, with the EPA providing a list of available and approved techniques for compounds of concern. The American Public Health Association, American Water Works Association, and Water Environmental Federation publish "Standard Methods for the Examination of Water and Wastewater", an extensive treatise on water analysis methodology. Most analytes require a two-step technique: chemical separation followed by analytical spectroscopy. This two-step approach is essential when a mixture is considered. The combination of signals from multiple analytes will wash out the signal from any individual compound. Consequently, field samples are frequently sent to a laboratory for chromatographic separation followed by some form of analytical detection.

Separation is critical for reliable, accurate detection. But, without adequate detection techniques, separations are of little value. A variety of methods are used in water analysis. Ultraviolet-visible (UV/vis) spectroscopy is popular, as the technique is simple and quantitative. However, UV/vis cannot detect material concentrations much better than one part per million, limiting its value to high-level screening of basic ions or gross contaminants. Other optical methods such as fluorescence, refractive index measurements, or colorimetry either require specialized chromaphores or similarly lack sensitivity.

Mass spectrometry (MS) is a widely used and popular approach with the ability to measure at the required sensitivities. MS is a standard add-on to liquid chromatography systems (LC-MS), although at a cost of tens of thousands of dollars. MS requires ionization of the analyte of interest, breaking the compound into various subcomponents. These charged components pass through a magnetic field and are differentially deflected onto a detector array. The distribution across the detector array is a function of the charge-to-mass ratio. Various derivatives that are more sensitive or more accurate have been developed, but it is possible to detect sub-ppb using MS. On the other hand, the disadvantages of MS are 1) high cost, and 2) the impracticality of developing a portable, handheld system. These limitations keep MS as a laboratory instrument for trained operators.

What is needed is a portable, rapid measurement analysis instrument to allow water suppliers to 1) determine more quickly which compounds are present, 2) choose remediation steps, 3) add specific monitoring of ground and surface water, 4) increase studies of the human health effects of specific pharmaceuticals, and 5) eliminate the source through targeted public educating on proper disposal of prescription and non-prescription drugs.

SUMMARY OF THE INVENTION

The present invention provides a microfluidic separation device that includes a sample channel having a first sample channel region and a second sample channel region, where a cross-section of the first sample channel region is smaller than a cross-section of the second sample channel region. The invention further includes a detection region having a first detection region and a second detection region, where a cross-section of the first detection region is larger than a cross-section of the second detection region and the second sample channel region is connected to the first detection region. Additionally, the invention includes a marker input channel disposed to input markers into the second sample channel region, where the markers are larger than the cross-section of the first sample channel region and the cross-section of the second detection region, where the markers collect in the first detection region.

According to one aspect of the invention, the markers have a size in a range of 10 nm to 10 μm.

In another aspect, the markers move when subject to forces such as electroosmosis, electrophoresis, fluid pressure, moveable wall pressure, undulary electroosmosis, undulary electrophoresis, undulary fluid pressure or undulary moveable wall pressure.

In another aspect of the invention, the markers are can be gold particles, copper particles, silver particles, fluorescent particles, magnetic particles, particles having binding chemistry, latex particle, polystyrene particles or quantum dots.

In a further aspect of the invention, the second detection region includes a sieve structure having openings that are smaller than the markers.

In yet another aspect of the invention, the detection region can be flexible material that is operably disposed to form the first sample channel region and the second detection channel region.

BRIEF DESCRIPTION OF THE FIGURES

The objectives and advantages of the present invention will be understood by reading the following detailed description in conjunction with the drawing, in which.

DETAILED DESCRIPTION OF THE INVENTION

Although the following detailed description contains many specifics for the purposes of illustration, anyone of ordinary skill in the art will readily appreciate that many variations and alterations to the following exemplary details are within the scope of the invention. Accordingly, the following preferred embodiment of the invention is set forth without any loss of generality to, and without imposing limitations upon, the claimed invention.

The current invention provides a microfluidic separation device that is useful for surface-enhanced Raman spectroscopy (SERS) and other detection methods. Raman spectroscopy in general provides a chemical signature for a compound, but the Raman signal is generally too weak for part-per-billion detection levels. However, when a metallic nanoparticle that is smaller than the wavelength of light is introduced into the sample, the illuminating electric field will create surface plasmon resonances if there are free electrons in the nanoparticle, where the nanoparticle can be gold, silver, or copper beads, for example. These oscillating charges create an enhanced local electric field along certain directions. This field results in a much stronger Raman response. SERS experiments are often characterized by "hot spot" regions. Here the SERS signal reaches single-molecule detection capabilities. These regions are most likely due to nanoparticle alignments that create even larger electric field enhancements.

Using SERS for analyte detection has been under study. It is believed the large signal enhancement creates new opportunities to measure very small concentrations: picomolar, femtomolar, and potentially even single molecules. The challenge with SERS is creating an interaction between the analyte and the metal surface. The highest-sensitivity studies rely upon binding events to bring the molecules into close contact. While very sensitive, this approach is limited to measuring a previously decided set of analytes for which the nanoparticles are prepared. The binding does not need to be specific; for example, treatments with octadecylthiol have been used successfully for SERS on planar substrates.

Figure 1:
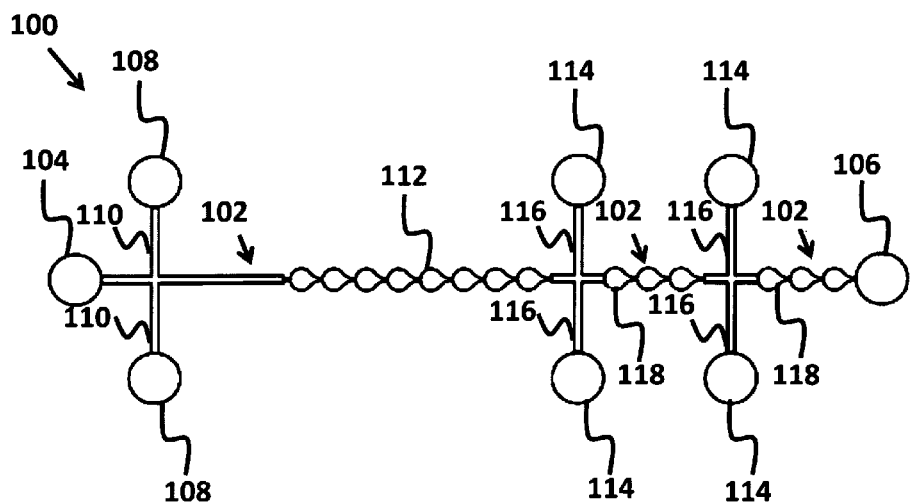
FIG. 1 shows a top view of one embodiment of the microfluidic mixing device according to the present invention.

According to one aspect of the current invention, a sensitive detection system incorporated in a portable device is provided. The invention includes packing sections along a microfluidic separation channel with nanoparticles, for example gold nanoparticles, at a high density. The invention creates many hot spots simply through particle density. The invention uses microfluidic delivery and narrow channel geometries to trap signal-enhancing particles at a detection location within a longer separation channel. Referring now to the figures, FIG. 1 shows a top view schematic of a microfluidic separation device 100 having a main channel 102 spanning from a fluid input 104 to a fluid output 106. The microfluid separation device 100 includes at least one sample loading port 108 connected to the main channel 102 by a sample loading channel 110. Separation regions 112 are disposed down stream from the sample loading channel 110. The invention further includes at least one detection particle loading port 114 connected to the main channel 102 by a detection particle channel 116. At least one detection region 118 is disposed down stream from the detection particle channel 116. As shown in the exemplary device of FIG. 1, the main channel 102 is intersected by two perpendicular sample loading channels 110 to load the sample under study into the main channel 102, while the detection particle channel 116 is for loading the nanoparticle markers into the main channel 102.

Figure 2:
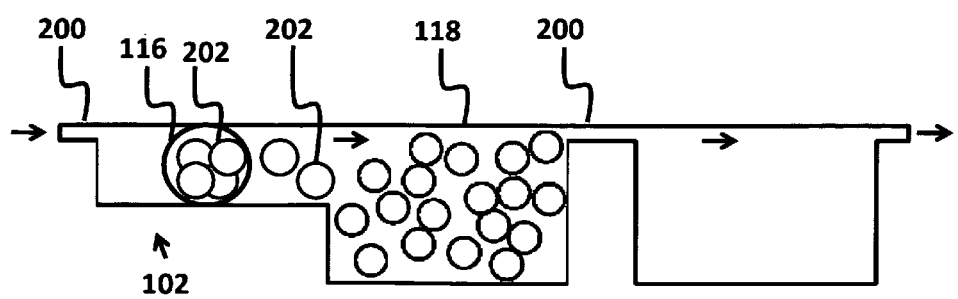
FIG. 2 shows a side cutaway view of a detection region of the microfluidic mixing device in FIG. 1 according to the present invention.

FIG. 2 shows a side view of a detection region 118 of the microfluidic mixing device 100 in FIG. 1 according to the present invention. Proximal to the intersection of the detection particle channels 116 and the main channel 102 are geometric constrictions 200 that trap the nanoparticles 202 within the detection region 118. Further shown are arrows to indicate the flow direction of the fluid within the microfluid separation device 100. The fluid moves the nanoparticles 202 along the flow path to compact them within the detection region 118.

The current invention relies purely on proximity by creating a region densely packed nanoparticles 202. According to one exemplary structure of the invention, tight packing density (close-packed spacing) predicts a maximum volume ratio of 74% spherical nanoparticles for a microfluidic channel region 118 that is 50 μm in length and has a 25 μm width and depth, loaded with 40-nm gold nanoparticles 202, this type of volume packing will have a surface area nearly 700 times greater than the surface area of the channel region. Furthermore, the narrow regions between nanoparticles 202 with the non-linear path through the matrix will increase interactions. The current invention provides a sensitivity requirement of detecting materials in parts per billion.

In the base configuration of the current invention, included is a main channel 102 with at least one crossing sample loading channel 110 and at least one nanoparticle loading channel 116, and the detection region 118. The detection region 118 has geometric constraints 200 that prevent particles 202 of a certain size from entering the main channel 102 in either direction, or from continuing past the detection channel 118. The nanoparticles 202 may be metallic, such as gold, copper, silver, fluorescent particles, magnetic particles, particles having binding chemistry, latex particle, polystyrene particles or quantum dots for surface-enhanced Raman scattering. According to one aspect, the particles are on the order of 10 nm to 10 μm. The particles 202 may also be fluorescent beads designed to bind with an analyte of interest for an ELISA-type signaling approach. These particles can be loaded using any type of fluid driving mechanism such as electroosmosis, electrophoresis, fluid pressure, moveable wall pressure, undulary electroosmosis, undulary electrophoresis, undulary fluid pressure or undulary moveable wall pressure. Note that between the sample input channel 110 and detection region 118 can be a separation region 112 that isolates individual compounds (undulary electroosmosis, electrophoresis, or chromatography) before entering the detection region 118.

It should be apparent there are many geometries may be used to create these detection regions 118. The constrictions 200 can occur in the vertical direction, reducing the detection region 118 size from top to bottom. This approach requires etching short depths or sacrificial layers. The constrictions 200 can also occur in the horizontal direction, which would rely upon lithographic abilities to define the narrowest gaps.

According to one aspect of the invention, the Raman signal can be further increased by using chemistries, both non-specific and specific, to bind analytes to the nanoparticles 202. With over a billion nanoparticles 202 in each detection region 118, along with multiple detection regions 118, a separation column 102 could hold a large number of modified nanoparticles 202. For example, with five detection regions 118, each holding two hundred different bindings, this system 100 could detect one thousand compounds while maintaining greater than five million nanoparticles 202 per region.

Figure 3:
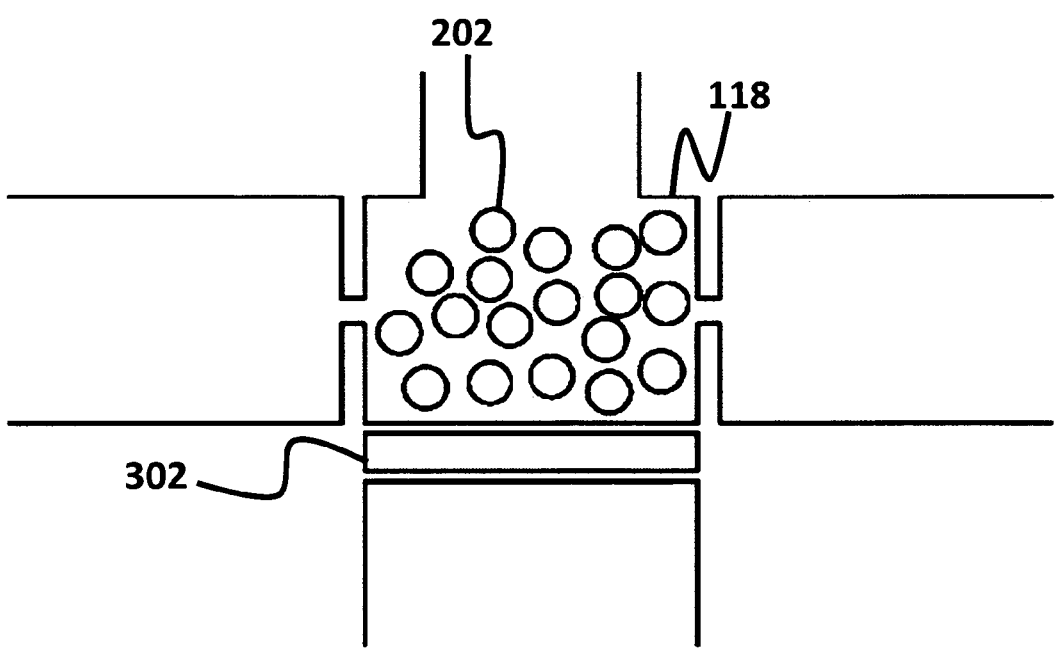
FIG. 3 shows a top view of a detection region with a liquid sieve at one end according to the present invention.

FIG. 3 shows an alternate embodiment 300 of the invention, where the detection region 118 includes a sieve material 302 that allows the carrying fluid to continue moving but stops the detection particles 202. For example, a molecular sieve will allow water to pass under pressure through atomic level openings in the material, but will block passage of larger particles.

Figure 4:
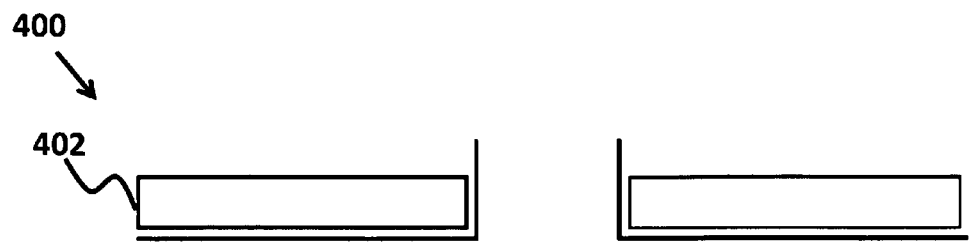
FIGS. 4a-4b show flexible microfluidic walls in an unconstructed state and in a constricted state according to the present invention.
Figure 4:
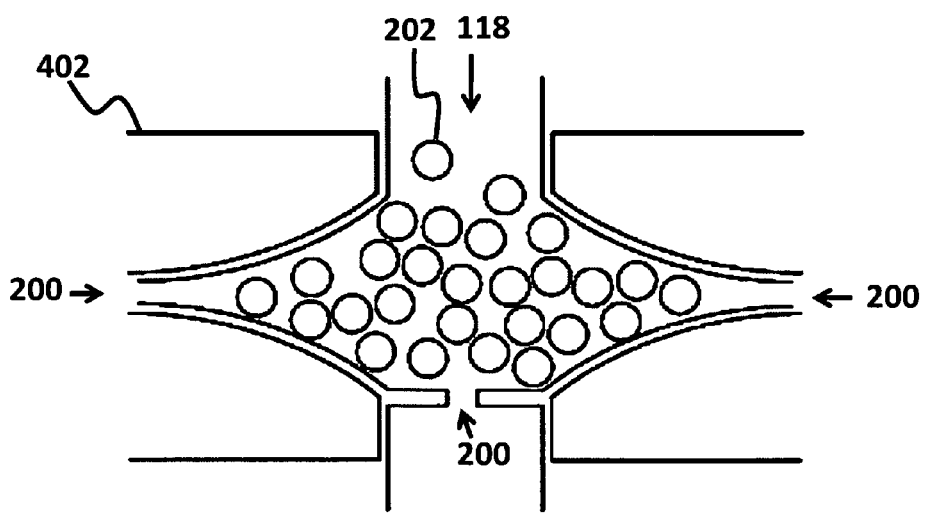

FIGS. 4a and 4b show another embodiment of the invention 400 that includes a reconfigurable detection region. According to the current embodiment 400 the main channel 102 can be constructed from a flexible material, such as silicone elastomers. If a bladder region 402 was placed in near proximity to the main channel 102, any pressure applied to the bladder 402 will expand into the main channel 102, and provide a constricting region 200 to the channel 102. This approach allows for detection regions 118 to be repeatedly created and released, thus allowing for repeated use with different detection particles. It also allows one generic design to use particles 202 of different sizes, as the channel can be configured for any size constriction.

Figure 5:
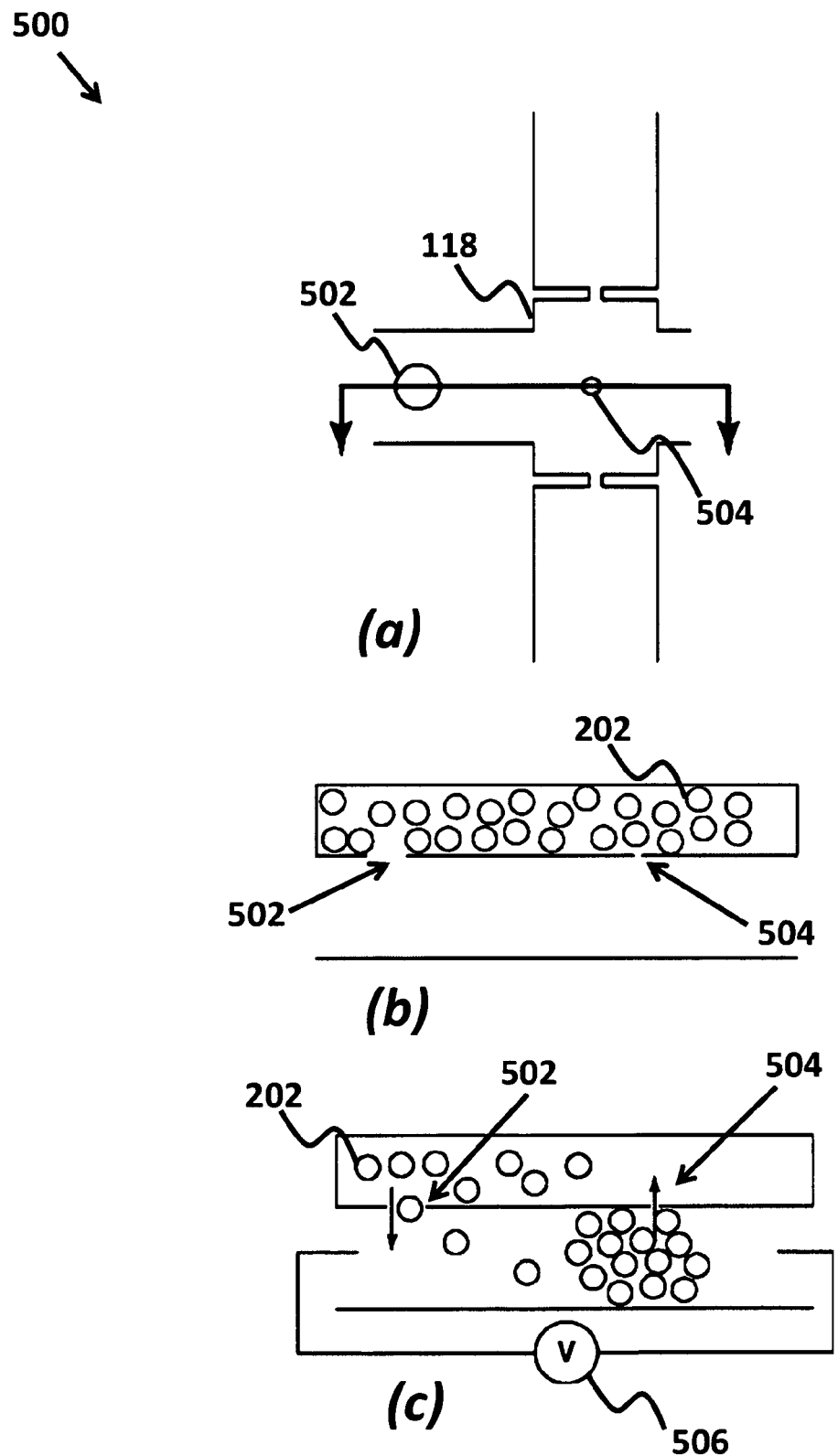
FIGS. 5a-5c show an alternative form of nanoparticle delivery according to the present invention.

FIGS. 5a-5c show a further embodiment 500 for supplying particles 202 to a detection region. FIG. 5a shows a top view of the current embodiment 500 that includes an annotation to indicate the centerline of the cutaway views in FIGS. 5b and 5c. According to the figures, a third dimension is considered. Here, the top surface of the detection region 118 contains a first aperture 502 that is large enough to pass particles 202 and a second aperture 504 that is smaller than the particles. When an electric potential 506 is applied along the detection region 118, the fluid and particles 202 will flow out of the first aperture 502 by electroosmosis. The fluid will flow back through the second aperture 504, but the particles 220 will not pass. This method creates local high density of particles 202 at the second aperture 504.

The present invention has now been described in accordance with several exemplary embodiments, which are intended to be illustrative in all aspects, rather than restrictive. Thus, the present invention is capable of many variations in detailed implementation, which may be derived from the description contained herein by a person of ordinary skill in the art. For example, the device may be injection molded, constructed of elastomers, or processed using semiconductor methods and materials. The channels may contain curved segments to extend their lengths or may have varying depths to encourage separation. The detection particles could combine multiple signaling and binding mechanisms, such as being magnetic and fluorescent to enhance optical detection within a magnetic field. All such variations are considered to be within the scope and spirit of the present invention as defined by the following claims and their legal equivalents.

What is claimed is:

1. A microfluidic separation device comprising:
    a. a sample channel, wherein said sample channel comprises a first sample channel region and a second sample channel region, wherein a cross-section of said first sample channel region is smaller than a cross-section of said second sample channel region;
    b. a detection region comprising a first detection region and a second detection region, wherein a cross-section of said first detection region is larger than a cross-section of said second detection region and said second sample channel region is connected to said first detection region;
    c. an illuminating electric field;
    d. Raman-scattering nanoparticles, wherein said Raman-scattering nanoparticles comprise surface plasmon resonances for detection when illuminated by said illuminating electric field, wherein said surface plasmon resonances create an enhanced local electric field along specific directions, wherein said enhanced local electric field results in an enhanced Raman response; and
    e. a Raman nanoparticle input channel disposed to input said Raman-scattering nanoparticles into said second sample channel region, wherein said Raman-scattering nanoparticles are larger than said cross-section of said first sample channel region and larger than said cross-section of said second detection region, wherein said Raman-scattering nanoparticles are disposed to collect in said first detection region to form region of densely packed said Raman-scattering nanoparticles.

2. The microfluidic separation system of claim 1, wherein said Raman-scattering nanoparticles have a size in a range of 10 nm to 10 µm.

3. The microfluidic separation system of claim 1, wherein said Raman-scattering nanoparticles move when subject to forces selected from the group consisting of electroosmosis, electrophoresis, fluid pressure, moveable wall pressure, undulary electroosmosis, undulary electrophoresis, undulary fluid pressure and undulary moveable wall pressure.

4. The microfluidic separation system of claim 1, wherein said Raman-scattering nanoparticles are selected from the group consisting of gold particles, copper particles, silver particles, magnetic particles, particles having binding chemistry, and quantum dots.

5. The microfluidic separation system of claim 1, wherein said second detection region comprises a sieve structure having openings smaller than said Raman-scattering nanoparticles.

6. The microfluidic separation system of claim 1, wherein said detection region comprises flexible material, wherein said flexible material is operably disposed to form said first sample channel region and said second detection channel region.

* * * * *